United States Patent
Deng et al.

(10) Patent No.: US 9,556,128 B2
(45) Date of Patent: Jan. 31, 2017

(54) PREPARATION METHOD FOR ACRYLATE COMPOUND

(71) Applicants: NUTRICHEM COMPANY LIMITED, Beijing (CN); SHANGYU NUTRICHEM CO., LTD., Zhejiang (CN)

(72) Inventors: Xufang Deng, Beijing (CN); Wenjun Wang, Beijing (CN); Jianwei Chen, Beijing (CN); Yongchang Zhao, Beijing (CN); Jianhong Chi, Beijing (CN); Long Wang, Beijing (CN); Hua'nan You, Beijing (CN)

(73) Assignees: NUTRICHEM COMPANY LIMITED, Beijing (CN); SHANGYU NUTRICHEM CO., LTD., Shangyu (CN)

(*) Notice: Subject to any disclaimer, the term of this patent is extended or adjusted under 35 U.S.C. 154(b) by 0 days.

(21) Appl. No.: 14/778,336

(22) PCT Filed: Mar. 20, 2014

(86) PCT No.: PCT/CN2014/073732
§ 371 (c)(1),
(2) Date: Sep. 18, 2015

(87) PCT Pub. No.: WO2014/146581
PCT Pub. Date: Sep. 25, 2014

(65) Prior Publication Data
US 2016/0137611 A1 May 19, 2016

(30) Foreign Application Priority Data
Mar. 20, 2013 (CN) .......................... 2013 1 0090532

(51) Int. Cl.
| C07C 69/618 | (2006.01) |
| C07D 239/52 | (2006.01) |
| C07C 67/31 | (2006.01) |
| C07D 239/34 | (2006.01) |
| C07D 213/64 | (2006.01) |
| C07C 67/327 | (2006.01) |

(52) U.S. Cl.
CPC ............. *C07D 239/52* (2013.01); *C07C 67/31* (2013.01); *C07C 67/327* (2013.01); *C07D 213/64* (2013.01); *C07D 239/34* (2013.01)

(58) Field of Classification Search
CPC .................................................. C07C 69/618
See application file for complete search history.

(56) References Cited

U.S. PATENT DOCUMENTS

| 5,847,138 A | 12/1998 | Jones et al. |
| 6,162,916 A | 12/2000 | Whitton et al. |
| 8,124,761 B2 | 2/2012 | Whitton et al. |
| 2004/0152894 A1 | 8/2004 | Miyazawa et al. |
| 2008/0214587 A1 | 9/2008 | Whitton et al. |

FOREIGN PATENT DOCUMENTS

| CN | 1062139 A | * 6/1992 | ........... C07D 239/34 |
| CN | 1228086 A | * 7/1997 | ........... C07D 239/34 |
| CN | 102070538 A | 5/2011 | |
| CN | 102311392 A | 1/2012 | |
| EP | 2537832 A1 | 12/2012 | |
| IN | 276 CHE 2011 A | 11/2012 | |

OTHER PUBLICATIONS

International Search Report for International Application No. PCT/CN2014/073732, mailed Jun. 4, 2014, 5 pages.
Written Opinion for International Application No. PCT/CN2014/073732, mailed Jun. 4, 2014, 4 pages.
Zhang, et al., Bulletin of the Korean Chemical Society, vol. 33, issue 8, pp. 2627-2634, 2012.

* cited by examiner

*Primary Examiner* — Erich A Leeser
(74) *Attorney, Agent, or Firm* — Husch Blackwell LLP

(57) ABSTRACT

The present invention relates to a method for preparing an acrylate compound. The acrylate compound has a structure as shown in formula (I). The method includes: subjecting a compound with a structure of formula (II) or a mixture of compounds with structures of formula (I) and formula (II), and a catalyst to a contact reaction in the absence of an anhydride, and removing the resulting methanol by pressure reduced distillation during the contact reaction process. In the formulas (I) and (II), R is selected from one of: an alkoxy with a carbon number of 1-5, a substituent-containing phenoxyl with a carbon number of 6-20, a substituent-containing heteroaryloxy with a carbon number of 4-20, a substituent-containing heteroaryloxymethyl with a carbon number of 4-20, a substituent-containing phenoxymethyl with a carbon number of 5-20, and a substituent-containing alkyl with a carbon number of 2-20. According to the method for preparing an acrylate compound provided in the invention, the conversion rate and selectivity of the reaction can be substantially improved.

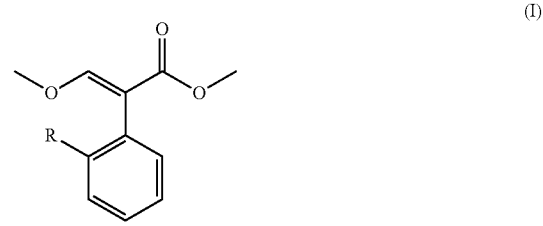

(I)

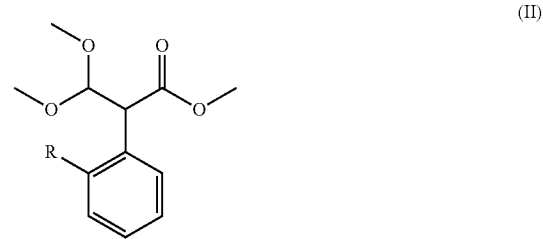

(II)

7 Claims, No Drawings

PREPARATION METHOD FOR ACRYLATE COMPOUND

FIELD OF THE INVENTION

The present invention relates to a preparation method for acrylate compound.

BACKGROUND OF THE INVENTION

Acrylate fungicides represented by azoxystrobin and picoxystrobin are a sort of new fungicides discovered and developed by Zeneca company, and can be represented by formula (I). A compound represented by formula (I) can be obtained from a compound represented by formula (II) by removing a methanol molecule.

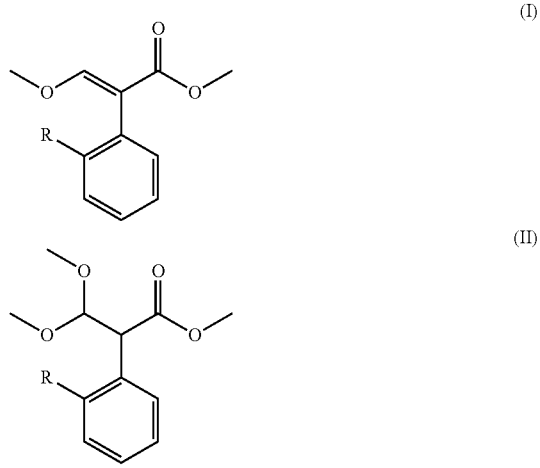

A compound represented by formula (III) is a type of acrylate compound, and can be obtained from a compound represented by formula (IV) by conversion.

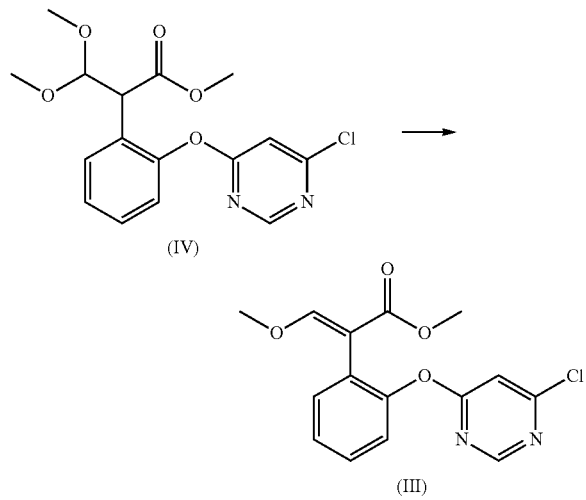

WO9208703A1 disclosed a method for implementing the above-mentioned conversion process. The method comprises: utilizing potassium bisulfate as a catalyst in the reaction at 250° C. to obtain the compound represented by formula (III). With that conversion method, the conversion ratio and selectivity of the reaction are not high enough.

U.S. Pat. No. 6,162,916A disclosed a method for conversion from the compound represented by formula (IV) to the compound represented by formula (III) by utilizing an acidic catalyst at 70-110° C. temperature in the presence of acid anhydride, acyl chloride, or 2-acetoxy benzonitrile.

CN102070538A disclosed a method for preparing the compound represented by formula (III) through a reaction between the compound represented by formula (IV) and acid anhydride with dimethyl sulfate as catalyst.

SUMMARY OF THE INVENTION

The inventor has found: methanol is produced in the reaction process for converting the compound with a structure represented by formula (II) to the compound with a structure represented by formula (I), and the quantity of methanol increases as the reaction proceeds. When the reaction proceeds to a specific level and the quantity of methanol produced in the reaction system is heavy, the existence of methanol will have impacts on the conversion ratio and selectivity of the reaction process. To overcome that problem, usually acid anhydride has to be added into the reaction system, allowing the methanol produced in the reaction to react with the acid anhydride to generate carboxylic acid, and thereby the methanol can be removed. However, the carboxylic acid generated in the reaction will react with methanol further to generate water, and the compound represented by formula (I) is unstable in an aqueous acid environment and will be hydrolyzed further to generate aldehyde, resulting in severely degraded conversion ratio and selectivity of the reaction. In addition, the acid anhydride has strong irritation and corrosivity, and may cause harms to the environment, besides damaging the reaction device.

Moreover, existing methods for preparing acrylate compounds represented by formula (I) usually require the presence of a solvent that doesn't participate in the reaction. The boiling point of the solvent usually should be 70-140° C., and usually may be selected from at least one of aromatic hydrocarbons (e.g., methyl benzene, chlorobenzene, o-xylene, m-xylene, etc.), alcohols (e.g., methanol, ethanol, etc.) and ketones (e.g., methyl isobutyl ketone, etc.). Since the reaction has to proceed in the presence of a solvent, on one hand, the cost for preparing the acrylate compound is increased; on the other hand, additional treatments must be made to the reaction mixture obtained in the reaction to remove the solvent in the reaction mixture; consequently, not only the reaction operations are more complex, but also a part of the product may be removed in the solvent removing operation owing to the complex operation steps, and thereby the yield ratio and selectivity of the reaction are affected; moreover, it should be noted that some solvents (e.g., aromatic hydrocarbons) may bring adverse impacts on the production environment and personal health, and is adverse to environmental protection, and at the same time may cause increased cost of environmental protection.

The object of the present invention is to overcome the following drawbacks in existing methods for preparing acrylate compounds represented by formula (I) in the prior art, and provides an innovative preparation method for acrylate compound.

Firstly, acid anhydride reacts with methanol in the system to produce carboxylic acid, and carboxylic acid will react with methanol further to produce water. The compound represented by formula (I) is unstable in an aqueous acid environment and will be hydrolyzed further to produce aldehyde, resulting in severely degraded conversion ratio and selectivity of the reaction; secondly, acid anhydride and carboxylic acid have a strong irritation, consequently, not only the personal health will be severely affected, but also the environment will be harmed by the three wastes produced in the reaction. In addition, acid anhydride has a strong corrosivity, and may cause damages to the reaction device and increased cost.

To realize the object described above, the present invention provides a preparation method for an acrylate compound that has a structure represented by formula (I) the method comprises: subjecting a compound with a structure represented by formula (II) or a mixture of a compound with a structure represented by formula (I) and a compound with a structure represented by formula (II) to have a contact reaction with a catalyst in the absence of acid anhydride, and removing the methanol produced in the contact reaction process by reduced pressure distillation;

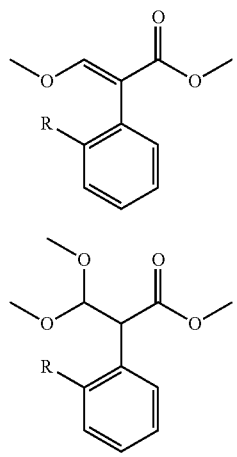

Wherein, R is selected from one of C1-C5 alkoxy, C6-C20 phenoxyl with a substituent group, C4-C20 heteroaryloxy with a substituent group, C4-C20 heteroaryloxymethyl with a substituent group, C5-C20 phenoxymethyl with a substituent group, and C2-C20 alkyl with a substituent group.

With the preparation method for acrylate compound provided in the present invention, the conversion ratio of the compound with a structure represented by formula (II) and the reaction selectivity of the compound with a structure represented by formula (I) can be improved significantly. Usually, with the method provided in the present invention, both the conversion ratio and the selectivity can be as high as 99% or above. The reason may be: in the method provided in the present invention, since the methanol generated in the reaction process wherein the compound with a structure represented by formula (II) is converted into the compound with a structure represented by formula (I) is removed by reduced pressure distillation (i.e., a part of the reaction product is removed), the reaction process always proceeds in the expected direction; in addition, since it is unnecessary to add acid anhydride into the reaction process, the degradation of conversion ratio and selectivity resulted from introduction of acid anhydride is avoided. Specifically, it can be seen from the results of example 1 and comparative example 1: in example 1, solvent and acid anhydride are not used, and the methanol generated in the reaction process is removed by reduced pressure distillation; whereas, in comparative example 1, acid anhydride is used and the reaction proceeds at atmospheric pressure; consequently, the conversion ratio and selectivity obtained in example 1 are as high as 99.6% and 99.5% respectively, which are apparently higher than those in comparative example 1.

In addition, it can be seen from the comparison between example 1 and example 12, the conversion ratio and selectivity of the reaction is higher when the method in the present invention is used without solvent.

With the method provided in the present invention, the reaction steps are simplified, the cost is reduced, and the impacts of solvent on the environment are avoided; in addition, since it is unnecessary to add acid anhydride in the reaction process, environmental pollution and equipment corrosion will not happen, the harm to environment and equipment brought by using acid anhydride in conventional methods is avoided. Therefore, the method provided in the present invention is more suitable for use in production at an industrial scale, and is applicable to prepare 2-substituted phenyl-3-methoxy acrylate fungicides, such as azoxystrobin and picoxystrobin intermediates.

DETAILED DESCRIPTION OF THE EMBODIMENTS

Hereunder the embodiments of the present invention will be detailed, with reference to the accompanying drawings. It should be appreciated that the embodiments described here are only provided to describe and explain the present invention, but shall not be deemed as constituting any limitation to the present invention.

The present invention provides a method for preparing an acrylate compound that has a structure represented by formula (I) the method comprises: subjecting a compound with a structure represented by formula (II) or a mixture of a compound with a structure represented by formula (I) and a compound with a structure represented by formula (II) to have a contact reaction with a catalyst in the absence of acid anhydride, and removing the methanol produced in the contact reaction process by reduced pressure distillation;

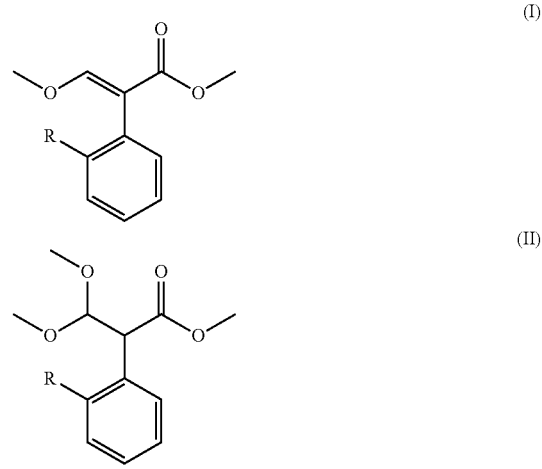

Wherein, R is selected from one of C1-C5 alkoxy, C6-C20 phenoxyl with a substituent group, C4-C20 heteroaryloxy with a substituent group, C4-C20 heteroaryloxymethyl with a substituent group, C5-C20 phenoxymethyl with a substituent group, and C2-C20 alkyl with a substituent group.

The heteroaryloxy can be pyridinyl with a substituent group or pyrimidinyl with a substituent group.

Preferably, R is 6-chloropyrimidinyl-4-oxy, 6-(2-cyanophenoxy)pyrimidinyl-4-oxy, chloromethyl or 2-((6-(trifluoromethyl)pyridinyl-2)-oxy)methyl; optimally, R is 6-chloropyrimidinyl-4-oxy.

According to the preparation method provided in the present invention, when the mixture contains the compound with a structure represented by formula (I), the mole ratio of the compound with a structure represented by formula (I) to the compound with a structure represented by formula (II) in the mixture can be 1:1.5-4, preferably, the mole ratio of the compound with a structure represented by formula (I) to the compound with a structure represented by formula (II) in the mixture is 1:2-3.5.

According to the preparation method provided in the present invention, the catalyst can be selected from at least one of sulfate compounds and sulfonic acid compounds.

Preferably, the catalyst is selected from at least one of dimethyl sulfate, diethyl sulfate, p-toluenesulfonic, and methanesulfonic acid.

In the preparation method provided in the present invention, to save the input and ensure the reaction can proceed smoothly, preferably, corresponding to 1 mol compound with a structure represented by formula (II), the usage amount of the catalyst is 0.005-0.2 mol; optimally, the usage amount of the catalyst is 0.02-0.1 mol. However, the present invention is not limited to this.

In the preparation method provided in the present invention, there is no particular restriction on the temperature and time of the contact reaction between the compound with a structure presented by formula (II) or a mixture of the compounds represented by formula (I) and (II) and the catalyst, which is to say, they can be determined according to the conventional conditions of reaction for preparing the compound represented by formula (I) from the compound represented by formula (II). The reaction temperature is preferably 90-145° C., more preferably 100-120° C.; the reaction time is preferably 60-240 min, more preferably 90-120 min.

To facilitate the reaction to proceed towards the direction of product formation so as to further improve the conversion ratio, selectivity, and efficiency of the reaction, the method provided in the present invention further comprises: controlling the pressure of the reaction system at a negative pressure in the reaction process, so as to continuously remove the methanol produced in the contact reaction process by reduced pressure distillation. The reaction pressure can be 100 kPa or below, preferably is 20-80 kPa. In the present invention, the pressure refers to absolute pressure.

In the reaction process provided in the present invention, the reactants can be stirred so that the components in the mixture can contact with each other fully and the heat transfer and mass transfer can be improved. The stirring can be carried out in any conventional stirring method in the art, such as anchor stirring, paddle stirring, or propeller stirring, etc.

In the preparation method provided in the present invention, the reaction situation can be monitored by liquid chromatography. After the reaction is completed, the stirring can be stopped, and allowing the reaction system to be cooled down to 20-30° C.

In the preparation method provided in the present invention, the reaction process that the compound with a structure represented by formula (II) is converted into the compound with a structure represented by formula (I) preferably proceeds without solvent. In that case, on one hand, the cost required for preparing the acrylate compound can be reduced; on the other hand, since it is unnecessary to remove the solvent from the reaction mixture, additional solvent removing operation for the obtained reaction mixture is unnecessary after the reaction is completed, and thereby the difficulty in reaction operation can be reduced, and the loss of a part of reaction product incurred by complex solvent removing operation steps can be avoided, and thereby the conversion ratio and selectivity of the reaction can be improved; in addition, the adverse impacts of partial reaction solvent on the production environment and personal health can be avoided.

In the method provided in the present invention, in order to obtain the compound with a structure represented by formula (I), the method may further comprise subsequent treatment steps for the product obtain from the reaction, such as cooling, washing, and crystallization, etc., after the reaction is completed.

Hereunder the present invention will be further detailed in examples.

In the following examples, the quantities of the reactants and product are measured with liquid chromatograph (Agilent 1200).

In the following examples, the conversion ratio and selectivity of the reaction are calculated with the following expressions:

Conversion ratio=(inputted mole quantity of the raw material−mole quantity of residual raw material in the product)/inputted mole quantity of raw material×100%

Selectivity=actual mole quantity of the target product/theoretical mole quantity of the target product×100%

Examples 1-11

The examples 1-11 are to describe the preparation method for acrylate compound provided in the present invention.

TABLE 1

| No. | R | Catalyst | (I) (mol) | (II) (mol) | Mole Ratio of Compound II to Catalyst | Temperature (° C.) | Pressure (kPa) | Time (min.) |
|---|---|---|---|---|---|---|---|---|
| Example 1 | 6-chloropyrimidinyl-4-oxy | Dimethyl sulfate | 0.05 | 0.14 | 1:0.06 | 110 | 50 | 105 |
| Example 2 | 6-chloropyrimidinyl-4-oxy | Dimethyl sulfate | 0.04 | 0.14 | 1:0.02 | 100 | 20 | 90 |
| Example 3 | 6-chloropyrimidinyl-4-oxy | Dimethyl sulfate | 0.07 | 0.14 | 1:0.1 | 120 | 80 | 120 |
| Example 4 | 6-chloropyrimidinyl-4-oxy | Dimethyl sulfate | 0.035 | 0.14 | 1:0.005 | 90 | 15 | 60 |
| Example 5 | 6-chloropyrimidinyl-4-oxy | Dimethyl sulfate | 0.09 | 0.14 | 1:0.2 | 145 | 100 | 240 |
| Example 6 | 6-chloropyrimidinyl-4-oxy | Diethyl sulfate | 0.05 | 0.14 | 1:0.6 | 110 | 50 | 105 |

TABLE 1-continued

| No. | R | Catalyst | (I) (mol) | (II) (mol) | Mole Ratio of Compound II to Catalyst | Temperature (° C.) | Pressure (kPa) | Time (min.) |
|---|---|---|---|---|---|---|---|---|
| Example 7 | 6-chloropyrimidinyl-4-oxy | Methanesulfonic acid | 0.05 | 0.14 | 1:0.06 | 110 | 50 | 105 |
| Example 8 | 6-chloropyrimidinyl-4-oxy | p-toluenesulfonic | 0.05 | 0.14 | 1:0.06 | 110 | 50 | 105 |
| Example 9 | 6-(2-cyanophenoxy)pyrimidinyl-4-oxy | Dimethyl sulfate | 0.05 | 0.14 | 1:0.06 | 110 | 50 | 105 |
| Example 10 | Chloromethyl | Dimethyl sulfate | 0.05 | 0.14 | 1:0.06 | 110 | 50 | 105 |
| Example 11 | 2-((6-(trifluoromethyl)pyridinyl-2-)oxy) methyl | Dimethyl sulfate | 0.05 | 0.14 | 1:0.06 | 110 | 50 | 105 |

Prepare the acrylate compound under the conditions shown in Table 1 respectively. The preparation steps are:

Load the reaction mixture into a dry flask equipped with a condenser. Stir to mix the mixture intensively, and heat up the reaction system to a corresponding reaction temperature, allow the reaction to proceed for a corresponding time while stirring continuously under a corresponding negative pressure, and remove the methanol generated in the reaction process continuously by reduced pressure distillation. After the reaction is completed, cool down the reaction mixture to 25° C. under nitrogen shielding, add ethyl acetate and water into the reaction mixture for washing, after stratification, condense the organic phase to a dry state, and add methanol into the residue so that the product can recrystallize; then, filter to obtain the target product. Measure the conversion ratio and selectivity of the reaction. The result is shown in Table 2.

Example 12

Prepare the acrylate compound according to the method described in example 1, the difference is that add 0.14 mol methyl benzene as the solvent into the reaction mixture. After the reaction is completed, first, remove the solvent by vacuum distillation; then, add ethyl acetate and water for washing, after stratification, condense the organic phase to a dry state, and add methanol into the residue so that the product can recrystallize; then, filter to obtain the target product. Measure the conversion ratio and selectivity of the reaction. The result is shown in Table.

Comparative Example 1

The comparative example is to describe the preparation method for acrylate compound in the prior art.

Prepare the compound represented by formula (III) according to the method described in example 1, the difference is that 1 mol acetic anhydride is added into the reaction mixture and the pressure of the reaction system is controlled at atmospheric pressure. After the reaction is completed, separate the product, and measure the conversion ratio and selectivity of the reaction. The result is shown in Table 2.

TABLE 2

| No. | Conversion Ratio (%) | Selectivity (%) |
|---|---|---|
| Example 1 | 99.6 | 99.5 |
| Comparative example 1 | 99.1 | 97.9 |
| Example 2 | 99.5 | 99.3 |
| Example 3 | 99.3 | 99.3 |
| Example 4 | 99.1 | 99.2 |
| Example 5 | 99.2 | 99.1 |
| Example 6 | 99.4 | 99.4 |
| Example 7 | 99.5 | 98.5 |
| Example 8 | 99.6 | 98.8 |
| Example 9 | 99.3 | 99.2 |
| Example 10 | 99.2 | 99.1 |
| Example 11 | 99.5 | 99.4 |
| Example 12 | 99.1 | 98.4 |

It can be seen from the data in Table 2: with the acrylate compound preparation method provided in the present invention, higher conversion ratio and higher selectivity of the reaction can be obtained. Specifically, it can be seen from the comparison between the result of example 1 and the result of comparative example 1: in the process of preparing the acrylate compound with the method provided in the present invention, both the conversion ratio and the selectivity of the reaction are superior to those of the preparation method in comparative example 1, in which acetic anhydride is added.

In addition, it can be seen from the comparison between the result of example 1 and the result of example 12: when the acrylate compound preparation process is executed without solvent, higher conversion ratio and higher selectivity of the reaction can be obtained.

Moreover, it can be seen from the comparison between the results of examples 1-3 and the results of examples 4-5: when the acrylate compound preparation process is executed under the preferred conditions (i.e., the mole ratio of the compound represented by formula (I) to the compound represented by formula (II) in the reaction mixture is 1:2-3.5, the mole ratio of the compound represented by formula (II) to the catalyst is 1:0.02-0.1, the reaction temperature is 100-120° C., the reaction pressure is 20-80 kPa, and the reaction time is 90-120 min.), higher conversion ratio and higher selectivity of the reaction can be obtained.

The preferred embodiments of the present invention are described above, but the present invention is not limited to the details in those embodiments. Those skilled in the art can make modifications and variations to the technical scheme of the present invention, without departing from the spirit of the present invention. However, all these modifications and variations shall be deemed as falling into the protection scope of the present invention.

In addition, it should be noted that each of the specific technical features described in above embodiments can be combined in any appropriate form, provided that there is no conflict. To avoid unnecessary repetition, the possible combinations are not described specifically in the present invention.

Moreover, different embodiments of the present invention can be combined freely as required, as long as the combinations don't deviate from the ideal and spirit of the present invention. However, such combinations shall also be deemed as falling into the protection scope of the present invention.

The invention claimed is:

1. A preparation method for an acrylate compound, the acrylate compound has a structure represented by formula (I) the method comprises:
subjecting a compound with a structure represented by formula (II) or a mixture of a compound with a structure represented by formula (I) and a compound with a structure represented by formula (II) to have a contact reaction with a catalyst that is an alkyl sulfate compound and in the absence of acid anhydride, and
removing the methanol produced in the contact reaction process by reduced pressure distillation,

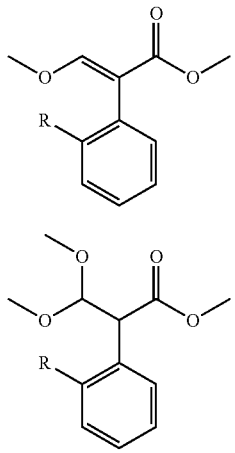

wherein, R is selected from one of C1-C5 alkoxy, C6-C20 phenoxyl with a substituent group, C4-C20 heteroaryloxy with a substituent group, C4-C20 heteroaryloxymethyl with a substituent group, C5-C20 phenoxymethyl with a substituent group, and C2-C20 alkyl with a substituent group.

2. The preparation method according to claim 1, wherein, R is 6-chloropyrimidinyl-4-oxy, 6-(2-cyanophenoxy)pyrimidinyl-4-oxy, chloromethyl, or 2-((6-(trifluoromethyl)pyridinyl-2-)oxy)methyl.

3. The preparation method according to claim 1, wherein, the mole ratio of the compound with a structure represented by formula (I) to the compound with a structure represented by formula (II) is 1:1.5-4.

4. The preparation method according to claim 1, wherein, corresponding to 1 mol compound with a structure represented by formula (II) used, the usage amount of the catalyst is 0.005-0.2 mol.

5. The preparation method according to claim 1, wherein, the catalyst is selected from at least one of dimethyl sulfate and diethyl sulfate.

6. The preparation method according to claim 1, wherein, the conditions of the contact reaction include: 90-145° C. for reaction temperature, 60-240 min for reaction time, and 100 kPa or lower for reaction pressure.

7. The preparation method according to claim 1, wherein, the contact reaction is carried out without solvent.

* * * * *